United States Patent
Li et al.

(10) Patent No.: US 11,111,236 B2
(45) Date of Patent: Sep. 7, 2021

(54) METHOD FOR PREPARING OXASPIROCYCLE DERIVATIVE, AND INTERMEDIATE THEREOF

(71) Applicant: JIANGSU HENGRUI MEDICINE CO., LTD., Jiangsu (CN)

(72) Inventors: Wenhai Li, Jiangsu (CN); Weixing Qi, Jiangsu (CN); Zhenjun Qiu, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/651,922

(22) PCT Filed: Sep. 27, 2018

(86) PCT No.: PCT/CN2018/107901
§ 371 (c)(1),
(2) Date: Mar. 27, 2020

(87) PCT Pub. No.: WO2019/062804
PCT Pub. Date: Apr. 4, 2019

(65) Prior Publication Data
US 2020/0308151 A1 Oct. 1, 2020

(30) Foreign Application Priority Data

Sep. 28, 2017 (CN) .......................... 201710896555.2

(51) Int. Cl.
*C07D 311/96* (2006.01)
*C07D 405/04* (2006.01)
*C07D 409/14* (2006.01)

(52) U.S. Cl.
CPC ......... *C07D 405/04* (2013.01); *C07D 409/14* (2013.01)

(58) Field of Classification Search
CPC ........................... C07D 311/96; A61K 31/352
USPC ........................................... 549/345; 514/456
See application file for complete search history.

(56) References Cited

U.S. PATENT DOCUMENTS 10,442,793 B2   10/2019   Li et al.

FOREIGN PATENT DOCUMENTS

WO   2012129495 A1   9/2012
WO   2017063509 A1   4/2017

OTHER PUBLICATIONS

Nov. 28, 2018 International Search Report issued in International Patent Application No. PCT/CN2018/107901.
Nov. 28, 2018 Written Opinion of the International Searching Authority issued in International Patent Application No. PCT/CN2018/107901.
Jakub Fichna et al., The Endomorphin System and Its Evolving Neurophysiological Role, Pharmacol. Rev. 2007; 59: 88-123.
Xiaotao Chen et al., Structure-Activity Relationships and Discovery of a G Protein Biased µ Opioid Receptor Ligand, [(3-Methoxythiophen-2-yl)methyl]({2-[(9R)-9-(pyridin-2-yl)-6-oxaspiro-[4.5]decan-9-yl]ethyl})amine (TRV130), for the Treatment of Acute Severe Pain, J. Med. Chem.2013, 56, 8019-8031.

*Primary Examiner* — Jeffrey H Murray
(74) *Attorney, Agent, or Firm* — Ice Miller LLP

(57) ABSTRACT

A method for preparing an oxaspirocycle derivative and an intermediate thereof are described. The method reduces reaction steps, improves reaction yield, is simple and easy to operate, and is favorable for industrial large-scale production.

15 Claims, No Drawings

METHOD FOR PREPARING OXASPIROCYCLE DERIVATIVE, AND INTERMEDIATE THEREOF

CROSS-REFERENCE TO RELATED APPLICATIONS

This application is a Section 371 of International Patent Application No. PCT/CN2018/107901, filed Sep. 27, 2018, which was published in the Chinese language on Apr. 4, 2019, under International Publication No. WO 2019/062804 A1, which claims priority under 35 U.S.C. § 119(b) to Chinese Patent Application No. 201710896555.2, filed Sep. 28, 2017, the disclosure of all of which are incorporated herein by reference in their entireties.

The present application claims the benefit of Chinese Patent Application No. CN201710896555.2 filed on Sep. 28, 2017, the content of which is incorporated herein by reference in its entirety.

FIELD OF THE INVENTION

The present disclosure relates to a method for preparing an oxaspirocyclic derivative and an intermediate thereof.

PRIOR ARTS

Postoperative pain is the most common acute pain. Commonly used drugs are opioids, e.g., Fentanyl, Morphine, Pethidine, Oxycodone, etc., the analgesic pharmacological activity of which is achieved by activating the Gαi protein receptor (μ opioid receptor, MOR) expressed on the cell membrane in the central nervous system and gastrointestinal tract and inhibiting hyperpolarization of nerve fibers. Opioid receptors are an important kind of G protein coupled receptors (GPCR) and are the targets to which endogenous opioid peptides and opioid drugs bind. The activated opioid receptors play a role in regulating the nervous system immunity and endocrine system. Currently, opioid drugs are the strongest and most commonly used central analgesics. Endogenous opioid peptides are naturally occurring opioid-like active substances in mammals. Currently, the known endogenous opioid peptides can be roughly classified into enkephalin, endorphin, dynorphin and nociceptin (*Pharmacol. Rev.* 2007; 59: 88-123). There are corresponding opioid receptors in the central nervous system, i.e., μ (MOR), δ (DOR), κ (KOR) receptors, etc. MOR is the target of opioid analgesics such as endogenous enkephalin and Morphine.

Long-term use of opioid drugs will cause side effects such as tolerance, respiratory depression and constipation, and it has been demonstrated that these side effects are closely related to the function of β-arrestin. In order to reduce the side effects of opioid drugs, the drugs can be designed based on the MOR negative β-arrestin oriented ligand, thereby reducing the β-arrestin mediated side effects and enhancing the therapeutic effect. In a study of oxaspirocyclic derivatives of the present disclosure used as selective MOR drugs, Trevena Inc. has found that the activity is lower when the aryl is substituted on the benzylic position (*J. Med. Chem.* 2013, 56, 8019-8031). Patent application WO2017063509A1 (publication date 2017 Apr. 20) discloses a MOR compound represented by formula (III) with a single configuration, the chemical name of which is (1S,4S)-4-ethoxy-N-(2-((R)-9-(pyridin-2-yl)-6-oxaspiro[4.5]decan-9-yl)ethyl)-1,2,3,4-tetrahydronaphthalen-1-amine. The method for preparing the compound is shown below:

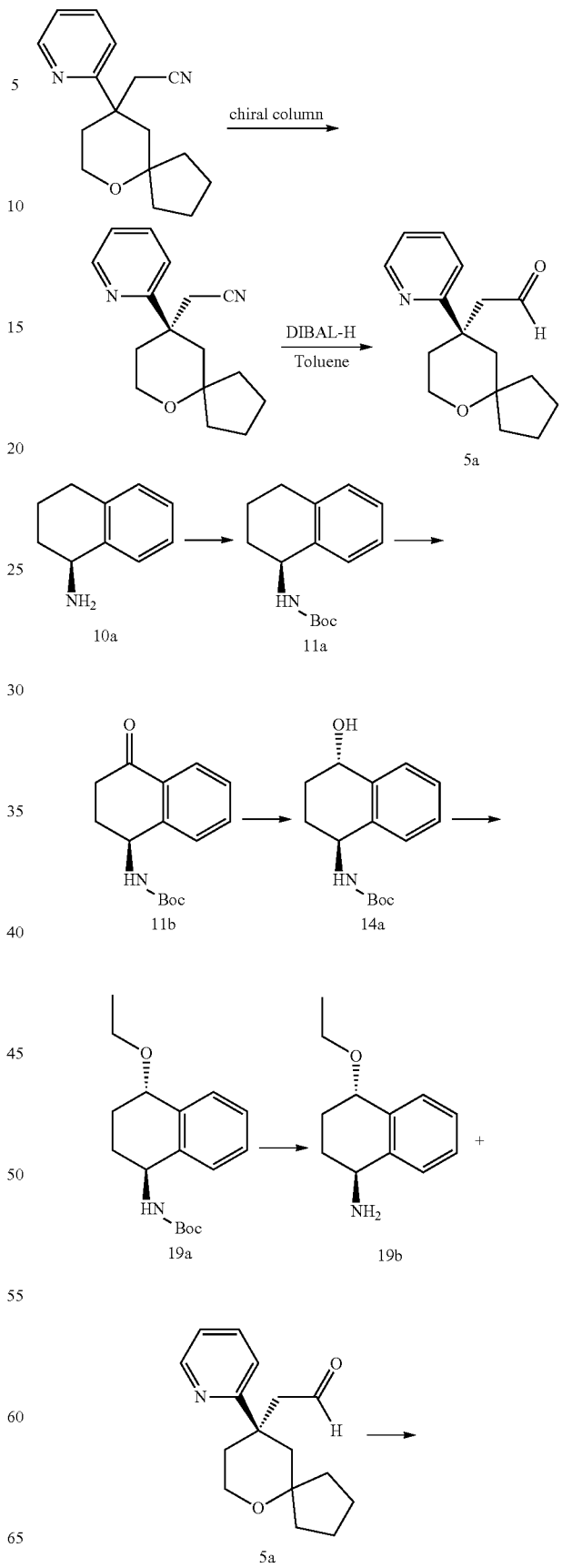

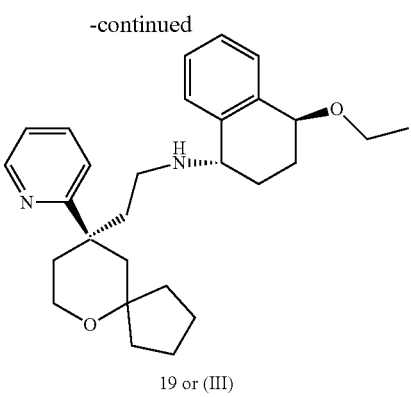

19 or (III)

This method has some drawbacks, such as small batch production, post-treatment method using chiral chromatography column purification, thin layer chromatography purification, and low yield, etc., wherein the yield for preparing compound 19 is only 35%. The reductant DIBAL used for preparing compound 5a is a dangerous and flammable reagent, and a lot of impurities are generated during the process, therefore, the method is not applicable to expanded industrial production and needs to be improved.

SUMMARY OF THE INVENTION

The present disclosure provides a method for preparing a compound represented by formula D1 or a salt thereof,

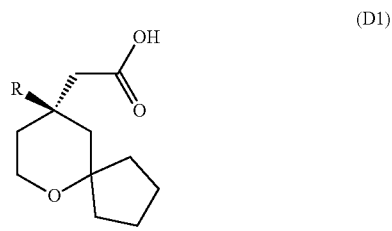

(D1)

the method comprising a step of chiral resolution of a compound represented by formula D or a salt thereof; wherein the method for the chiral resolution is preferably a chromatographic resolution method (e.g., chiral high performance liquid chromatography HPLC) or a chemical resolution method (e.g., using a chiral resolving agent for resolution),

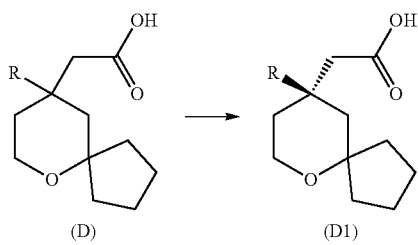

(D) (D1)

wherein, R is selected from aryl or heteroaryl, wherein the aryl or heteroaryl is optionally substituted by one or more substituents selected from the group consisting of alkyl, haloalkyl, halogen, amino, nitro, cyano, oxo, alkenyl, haloalkoxy, hydroxyalkyl, cycloalkyl, heterocyclyl, aryl, heteroaryl, $OR^3$, $C(O)R^3$, $C(O)OR^3$, $S(O)_mR^3$ and $NR^4R^5$;

$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are optionally substituted by one or more substituents selected from the group consisting of alkyl, halogen, hydroxyl, amino, nitro, cyano, alkoxy, hydroxyalkyl, cycloalkyl, heterocyclyl, aryl and heteroaryl;

each of $R^4$ and $R^5$ is independently selected from the group consisting of hydrogen, alkyl, alkoxy, hydroxyalkyl, hydroxyl, amino, carboxylic ester group, cycloalkyl, heterocyclyl, aryl and heteroaryl, wherein the alkyl, cycloalkyl, heterocyclyl, aryl and heteroaryl are optionally substituted by one or more substituents selected from the group consisting of alkyl, halogen, hydroxyl, amino, carboxylic ester group, nitro, cyano, alkoxy, hydroxyalkyl, cycloalkyl, heterocyclyl, aryl and heteroaryl; and m is 0, 1 or 2.

In some embodiments, the resolving agent used in the chiral resolution method is a basic chiral resolving agent, which can be S-phenylethylamine, quinidine, cinchonidine or arginine.

In some embodiments, the resolving agent used in the chiral resolution method is S-phenylethylamine.

Further, the method for preparing the compound represented by formula D1 or a salt thereof comprises a step of preparing the compound represented by formula D from a compound represented by formula E, and the reaction condition is preferably basic hydrolysis,

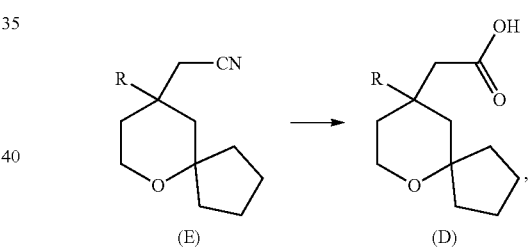

(E) (D)

wherein, R is as defined in the compound represented by formula D.

In some embodiments, the base used in the hydrolysis reaction is selected from the group consisting of sodium hydroxide, potassium hydroxide and lithium hydroxide, etc.

In some embodiments, the compound represented by formula D1 is shown as follows,

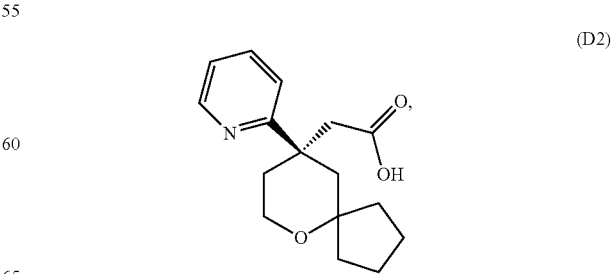

(D2)

the preparation method of which comprises:

(D-1) → (D2)

In some embodiments, the method for preparing the compound represented by formula D1 or a salt thereof comprises:

(D) →

(D1-1) →

(D1)

wherein, R is as defined in the compound represented by formula D.

In preferred embodiments, the method for preparing the compound represented by formula D2 or a salt thereof comprises:

(D-1) →

(D2-1) →

(D2)

The present disclosure also provides a compound represented by formula D1 or a salt thereof, (D1)

wherein, R is as defined above.

In some embodiments, the compound represented by formula D1 is shown as follows, (D2)

In some embodiments, the salt of the compound represented by formula D1 is shown as follows, (D1-1)

wherein, M is S-phenylethylamine, quinidine, cinchonidine or arginine.

In preferred embodiments, the salt of the compound represented by formula D1 is shown as follows,

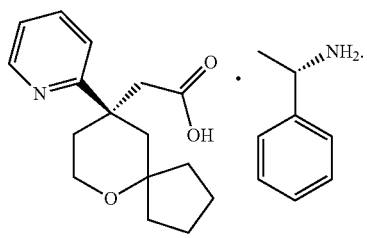

(D2-1)

The present disclosure also provides a method for preparing a compound represented by formula D1-1, the method comprising reacting a compound represented by formula D with a chiral resolving agent M to give the compound represented by formula D1-1; wherein the chiral resolving agent is preferably a basic chiral resolving agent, more preferably S-phenylethylamine, quinidine, cinchonidine or arginine,

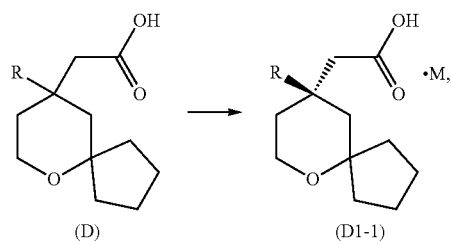

wherein, R is as defined in formula D1.

Further, the method for preparing the compound represented by formula D1-1 comprises:

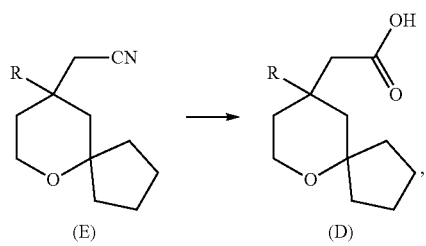

wherein, R is as defined in formula D1.

In some embodiments, R is

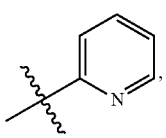 [SMILES: *c1ccccn1]

M is S-phenylethylamine, and the preparation method is shown as follows,

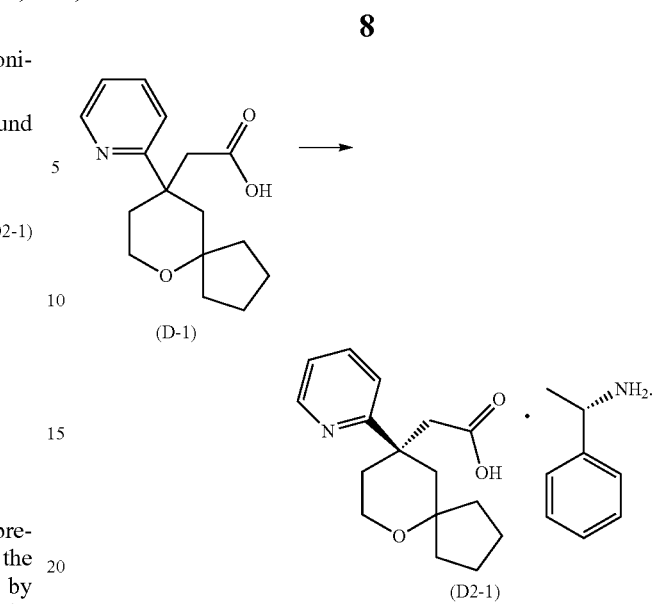

Further, the preparation method comprises:

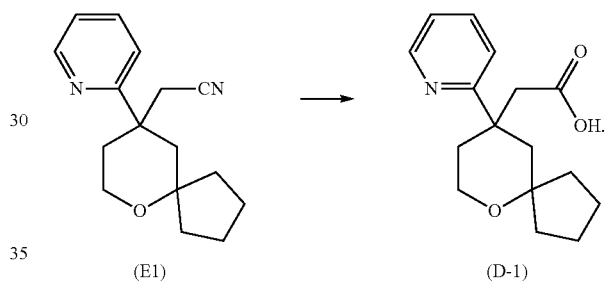

The present disclosure also provides a method for preparing a compound represented by formula B or a stereoisomer thereof, which comprises preparing the compound represented by formula B or a stereoisomer thereof from a compound represented by formula D or a stereoisomer thereof via an one-step reaction or a reaction of more than one steps,

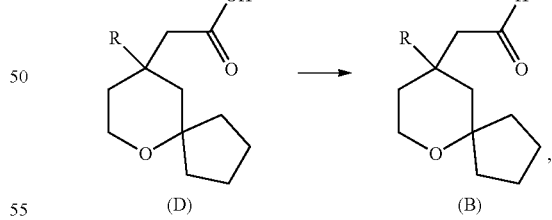

wherein R is as defined in the compound represented by formula D1, preferably

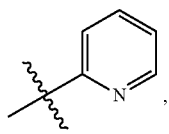

In some embodiments, the compound represented by formula B is shown as follows,

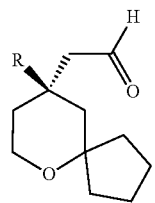
(B1)

the preparation method of which comprises:

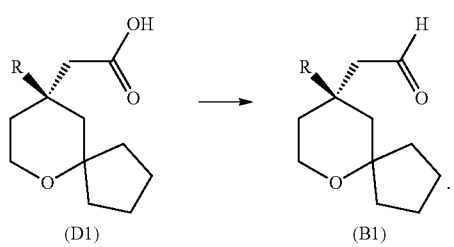
(D1)      (B1)

In the art, there are many well-known methods for reducing a compound containing a carboxyl group to obtain a compound containing an aldehyde group, and usually the compound containing an aldehyde group is prepared via a one-step reaction, a two-step reaction, or a reaction of more than two steps. The compound containing an aldehyde group is preferably prepared via a two-step reaction in the present disclosure.

In some embodiments, the method for preparing the compound represented by formula B or a stereoisomer thereof comprises:

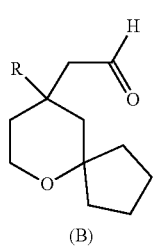
(B)

wherein, R is as defined in the compound represented by formula D1, preferably

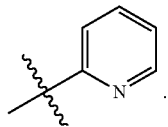 [SMILES: *c1ccccn1]

Preferably, in some embodiments, the compound represented by formula B or a stereoisomer thereof is shown as follows,

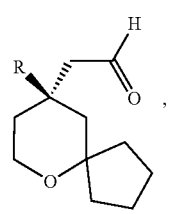
(B1)

the preparation method of which comprises

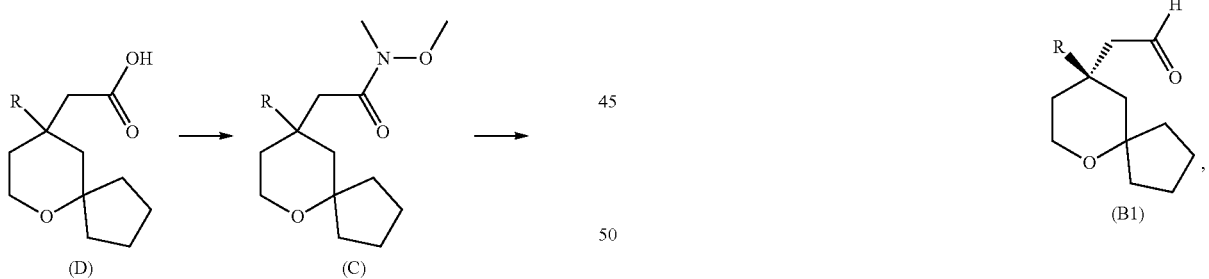
(D1)      (C1)

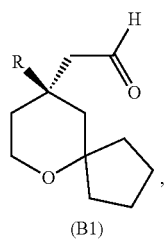
(B1)

wherein, R is preferably

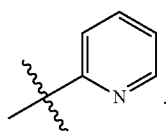 [SMILES: *c1ccccn1]

In some embodiments, the compound represented by formula B or a stereoisomer thereof is shown as follows,

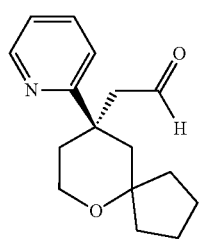

(B2)

the preparation method of which comprises:

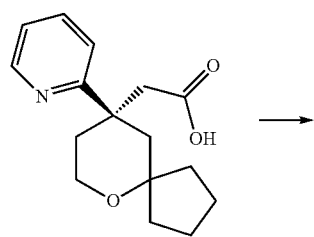

(D2)

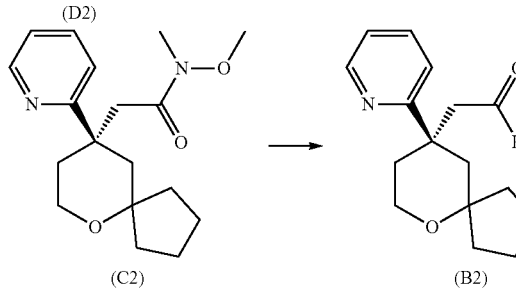

(C2) (B2)

Further, in some embodiments, the method for preparing the compound represented by formula B or a stereoisomer thereof comprises:

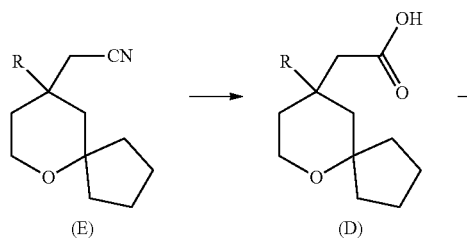

(E) (D)

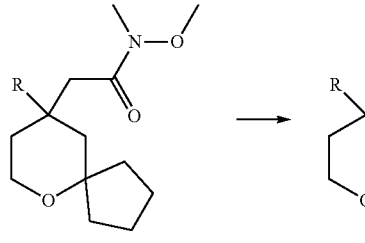

(C) (B)

wherein, R is as defined in the compound represented by formula D1.

In some embodiments, the method for preparing the compound represented by formula B or a stereoisomer thereof further comprises a step of the aforementioned method for preparing the compound represented by formula D1 or a salt thereof.

In some other embodiments, the compound represented by formula B or a stereoisomer thereof is

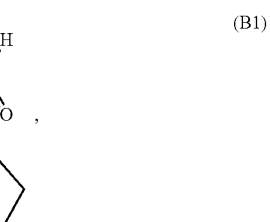

(B1)

the preparation method of which comprises:

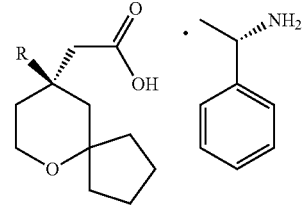

(E) (D)

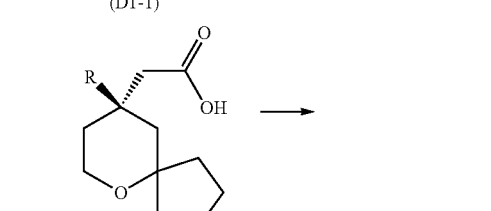

(D1-1)

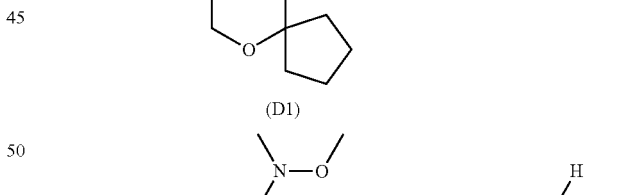

(D1)

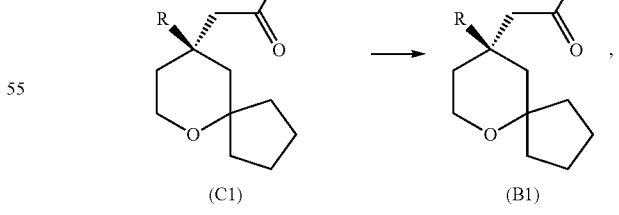

(C1) (B1)

wherein, R is as defined in the compound represented by formula D1.

In some other embodiments, the compound represented by formula B or a stereoisomer thereof is shown as follows,

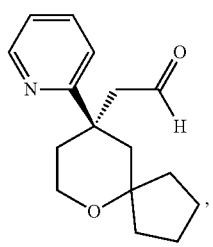

(B2)

the preparation method of which comprises:

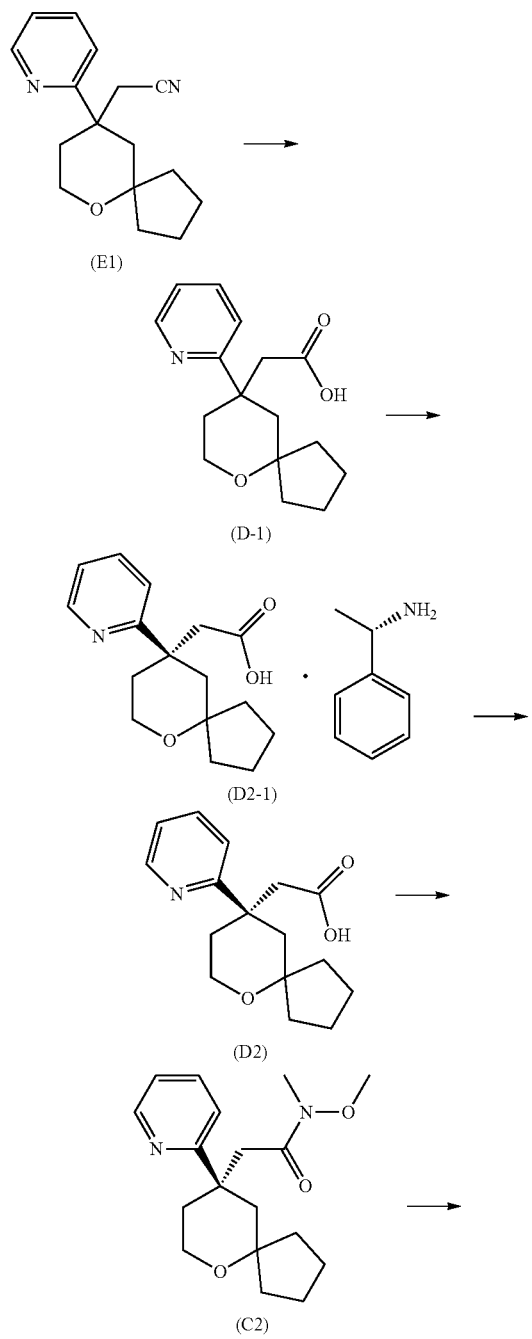

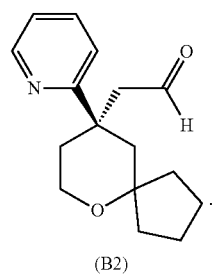

(B2)

The present disclosure also provides a compound represented by formula C,

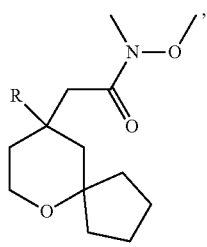

(C)

wherein, R is as defined in the compound represented by formula D1, preferably

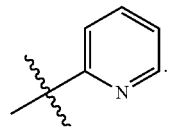 [SMILES: *c1ccccn1]

In some embodiments, the compound represented by formula C is shown as follows,

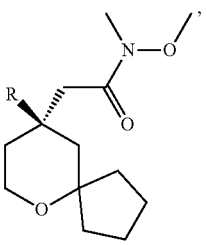

(C1)

wherein, R is as defined in the compound represented by formula D1, preferably

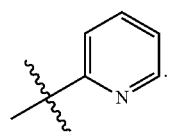 [SMILES: *c1ccccn1]

In some embodiments, the compound represented by formula C is shown as follows,

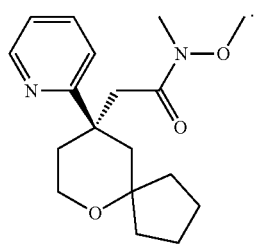

(C2)

The present disclosure also provides a method for preparing the compound represented by formula C, which comprises:

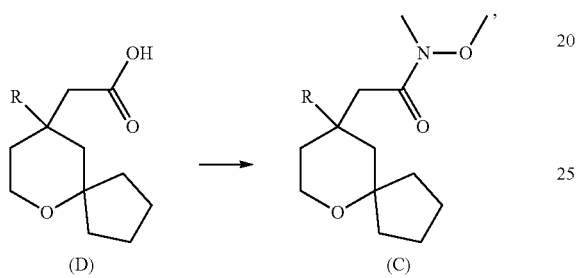

(D)    (C)

wherein, R is as defined in the compound represented by formula D1.

In some embodiments, the compound represented by formula C is shown as follows,

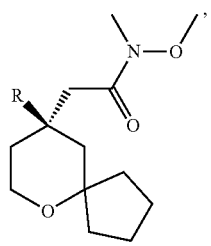

(C1)

the preparation method of which comprises:

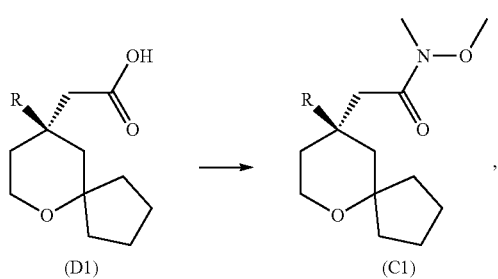

(D1)   (C1)

In some embodiments, the method for preparing the compound represented by formula C1 further comprises a step of the aforementioned method for preparing the compound represented by formula D1.

In some embodiments, the method for preparing the compound represented by formula C1 comprises:

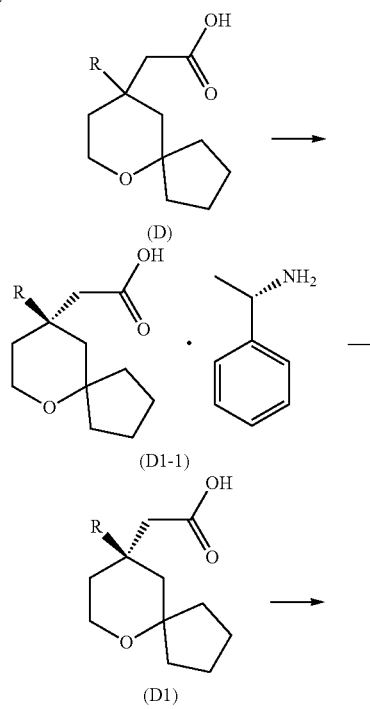

wherein, R is as defined in the compound represented by formula D1.

In some embodiments, the compound represented by formula C is shown as follows,

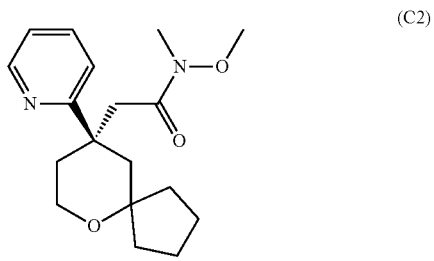 [SMILES: CON(C)C(=O)C[C@@]1(c2ccccn2)CCOC2(CCCC2)C1]

(C2)

the preparation method of which comprises:

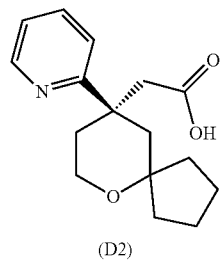

(D2)

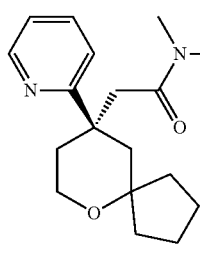

(C2)

In some embodiments, the method for preparing the compound represented by formula C2 further comprises a step of the aforementioned method for preparing the compound represented by formula D-1.

In some embodiments, the method for preparing the compound represented by formula C2 comprises:

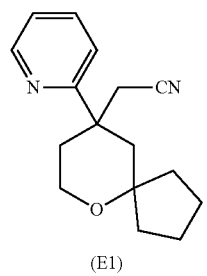

(E1)

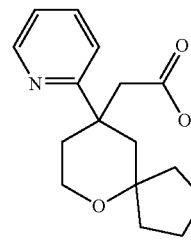

(D-1)

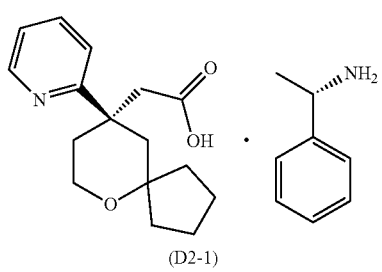

(D2-1)

The present disclosure also provides a method for preparing a compound represented by formula I or a salt thereof, which comprises reacting a compound represented by formula D or a stereoisomer thereof to give a compound represented by formula B or a stereoisomer thereof, and reacting the compound represented by formula B or a stereoisomer thereof with a compound represented by formula A or a stereoisomer thereof to give the compound represented by formula I,

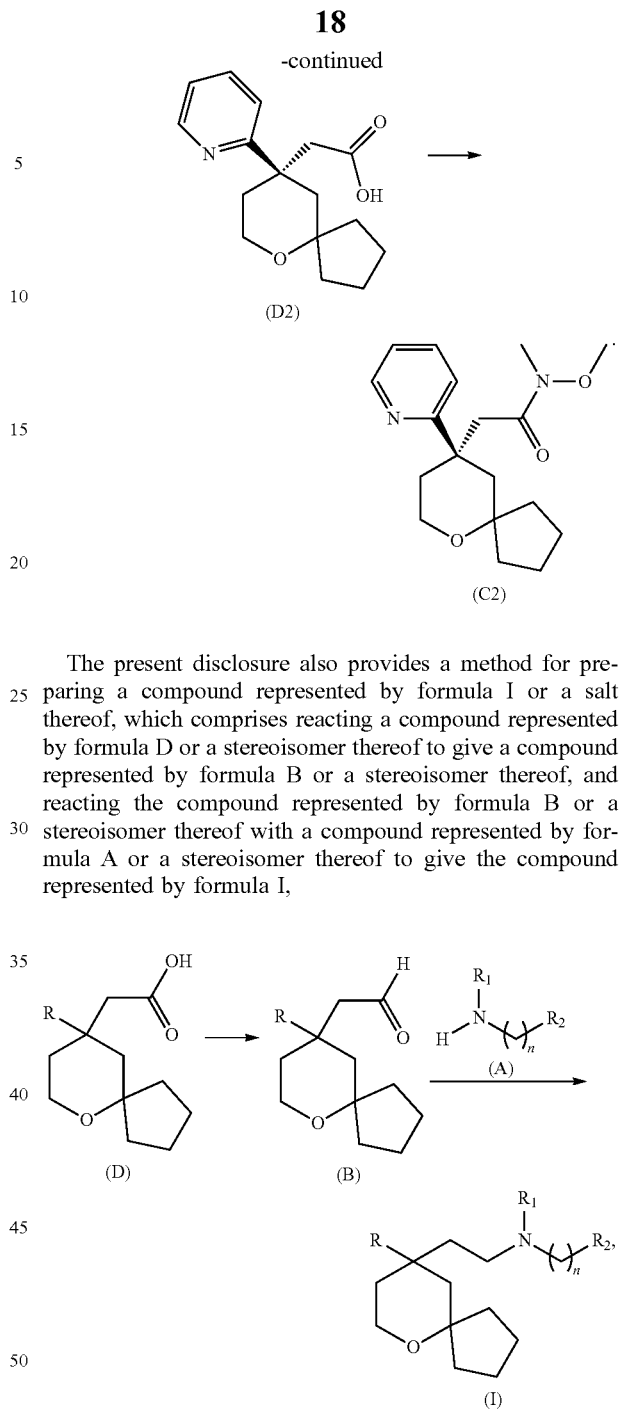

wherein, R1 is a hydrogen or an alkyl; R2 is an optionally substituted aryl or heteroaryl, and the substituent is selected from the group consisting of hydrogen, alkyl, haloalkyl, halogen, amino, nitro, cyano, oxo, alkenyl, haloalkoxy, hydroxyalkyl, cycloalkyl, heterocyclyl, aryl, heteroaryl, —OR3, —C(O)R3, —C(O)OR3, —S(O)mR3 and —NR4R5, wherein the alkyl, alkoxy, alkenyl, haloalkyl, cycloalkyl, heterocyclyl, aryl and heteroaryl are optionally substituted by one or more than one substituents selected from the group consisting of deuterium, alkyl, haloalkyl, halogen, amino, nitro, cyano, hydroxyl, alkoxy, haloalkoxy, hydroxyalkyl, cycloalkyl, heterocyclyl, aryl and heteroaryl; n is 0, 1, 2 or 3; R, R3, R4, R5 and m are as defined in the compound represented by formula D1.

In some embodiments, the method for preparing the compound represented by formula I or a salt thereof further comprises:

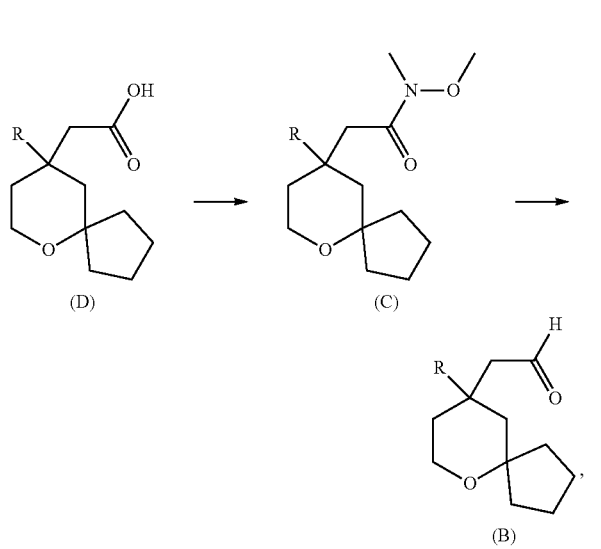

wherein, R is as defined in the compound represented by formula D1.

Further, the method for preparing the compound represented by formula I or a salt thereof further comprises:

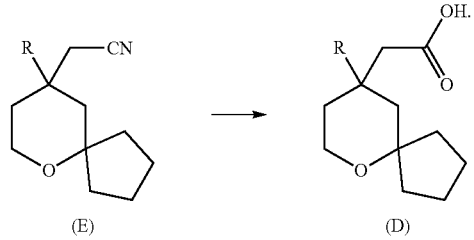

In some embodiments, the method for preparing the compound represented by formula I or a salt thereof further comprises a step of the aforementioned method for preparing the compound represented by formula D1 or a salt thereof.

In some embodiments, the method for preparing the compound represented by formula I or a salt thereof further comprises a step of the aforementioned method for preparing the compound represented by formula B or a stereoisomer thereof.

In some embodiments, the compound represented by formula I is shown as follows,

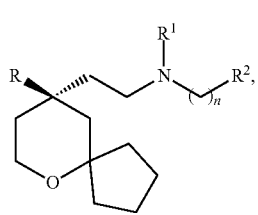

the preparation method of which comprises:

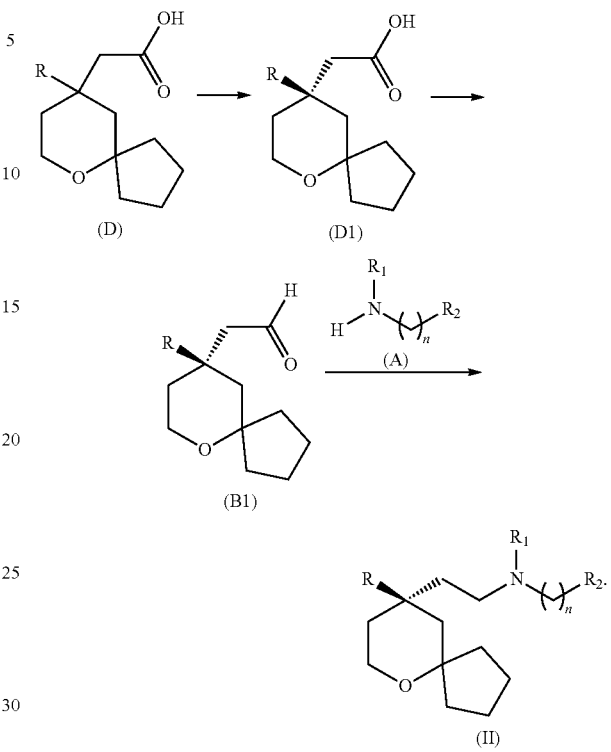

Further, the method for preparing the compound represented by formula II comprises:

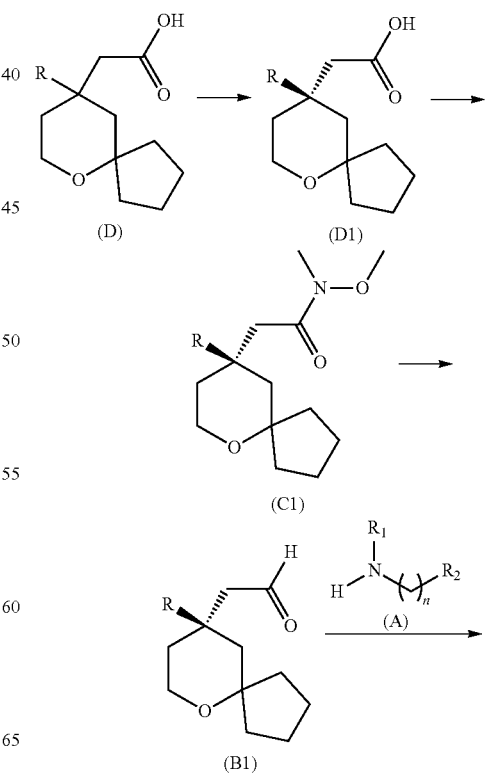

-continued

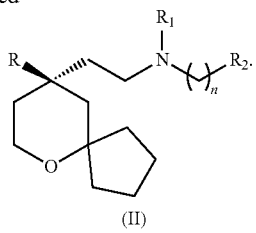

(II)

In some embodiments, the compound represented by formula I is shown as follows,

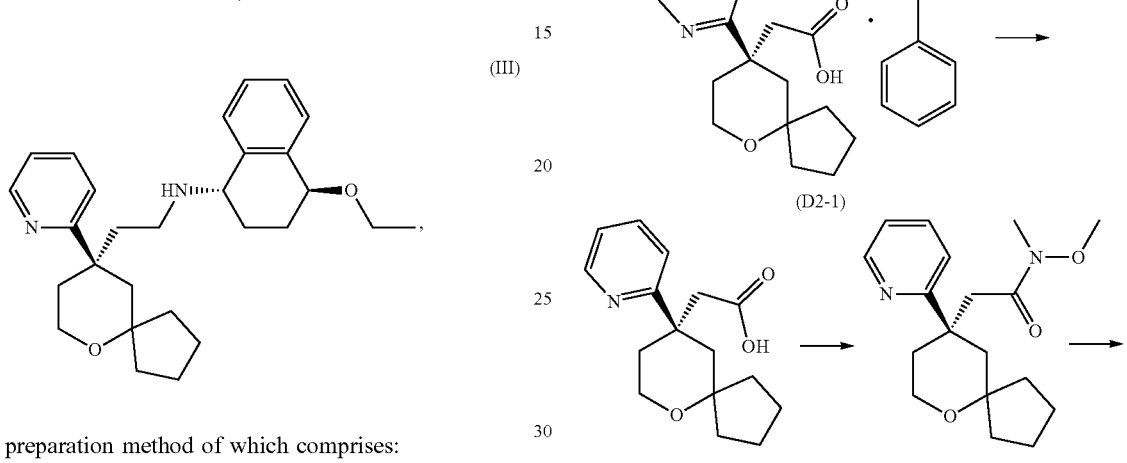

the preparation method of which comprises:

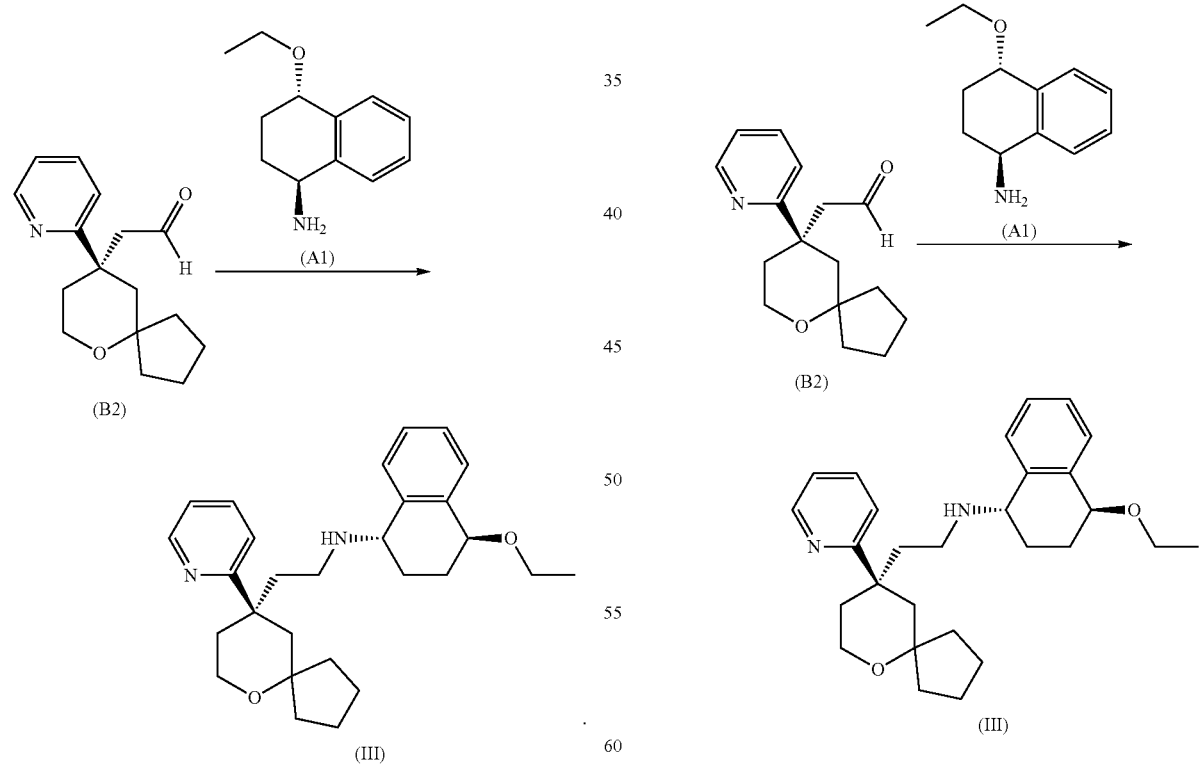

In some embodiments, the method for preparing the compound represented by formula III comprises:

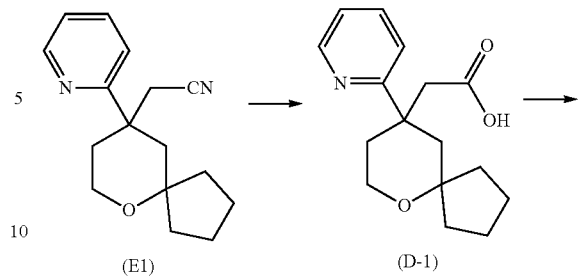

Preferably, the method for preparing the compound represented by formula III comprises:

Step One, Synthesis of Intermediate D-1 reacting the compound represented by the formula (E1) with a base in an organic solvent to undergo hydrolysis to give the compound represented by the formula D-1; the basic condition is preferably sodium hydroxide, potassium hydroxide or aqueous ammonia.

Step Two, Synthesis of Intermediate D2-1 reacting the compound represented by formula D-1 with a chiral resolving agent in an alcohol solvent to give the compound represented by formula D2-1; the chiral resolving agent is preferably a basic chiral resolving agent, more preferably S-phenylethylamine, quinidine, cinchonidine or arginine; the alcohol solvent is preferably methanol, ethanol or isopropanol.

Step Three, Synthesis of Intermediate D2 cleaving the compound represented by formula D2-1 under a basic condition to give the compound represented by the formula D2; the basic condition is preferably sodium hydroxide, potassium hydroxide or aqueous ammonia.

Step Four, Synthesis of Intermediate C2 reacting the compound represented by formula D2 with N,O-dimethylhydroxylamine hydrochloride, 1-(3-dimethyl-aminopropyl)-3-ethylcarbodiimide hydrochloride and 4-di-methylaminopyridine under a basic condition to give the compound represented by formula C2; the basic condition is preferably N,N-diisopropylethylamine, triethylamine or diisopropylamine.

Step Five, Synthesis of Intermediate B2 reacting the compound represented by formula C2 with a reductant to give the compound represented by formula B2; the reductant is preferably red aluminum.

Step Six, Synthesis of the Compound Represented by Formula (III)

reacting the compound represented by formula B2 with the compound represented by formula A1 to give the compound represented by formula II.

In some embodiments, the compound represented by formula I is shown as follows,

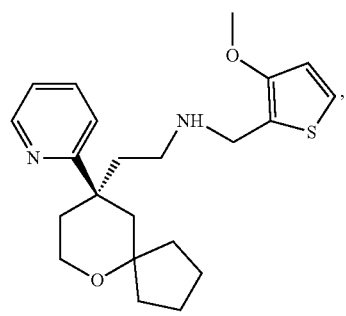

(IV)

the preparation method of which comprises:

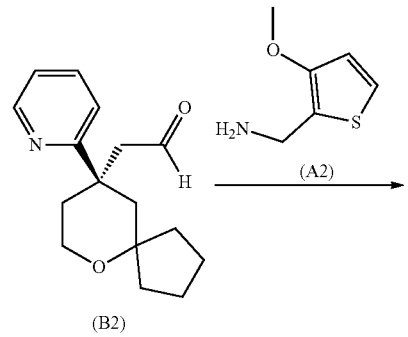

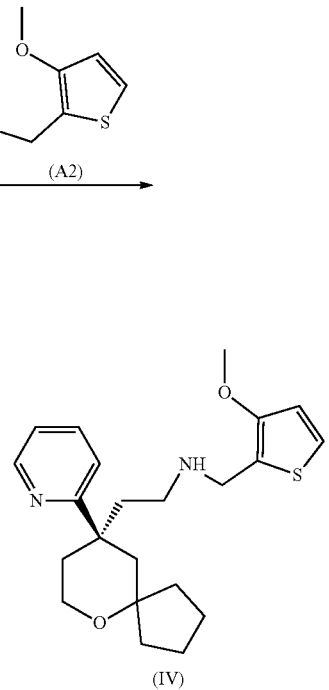

In some embodiments, the method for preparing the compound represented by formula IV comprises:

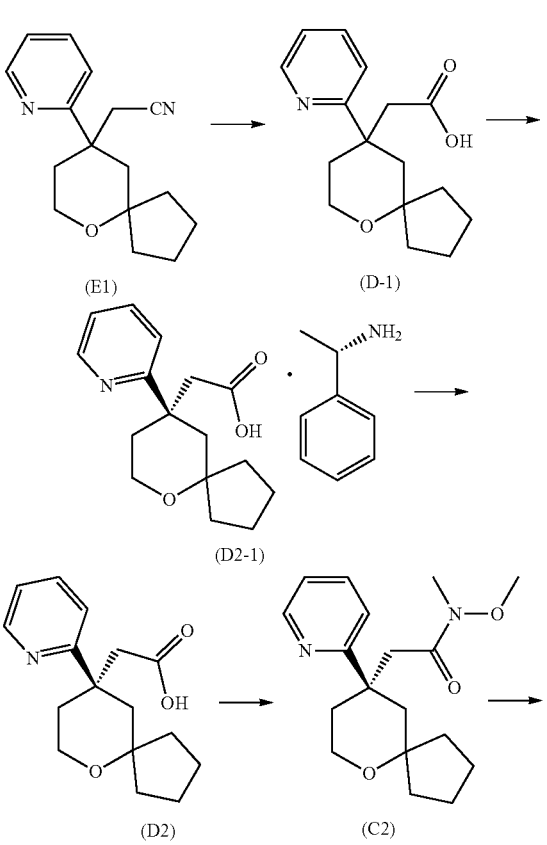

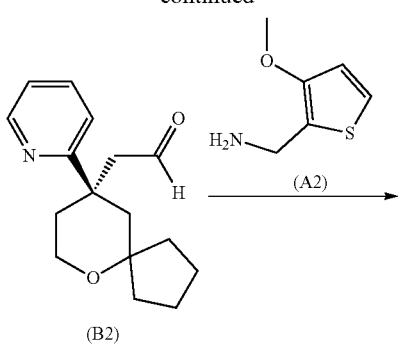

(B2)

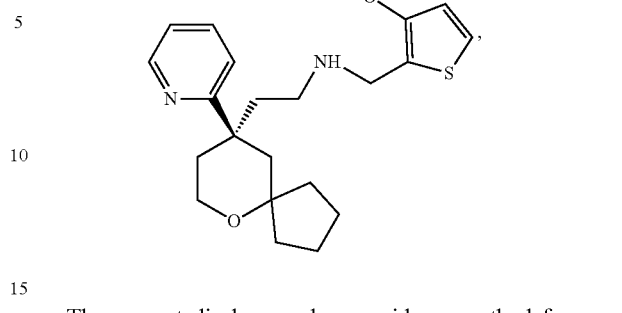

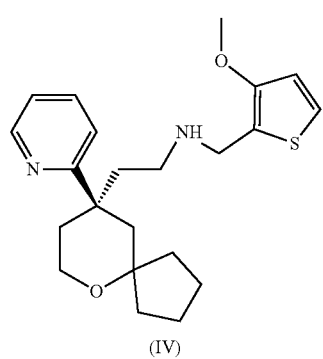

(IV)

The present disclosure also provides a use of the compound represented by formula D1, the compound represented by formula C or a salt thereof in the preparation of the compound represented by formula I,

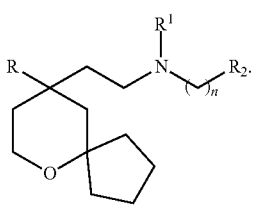

In some embodiments, the compound represented by formula I is shown as follows,

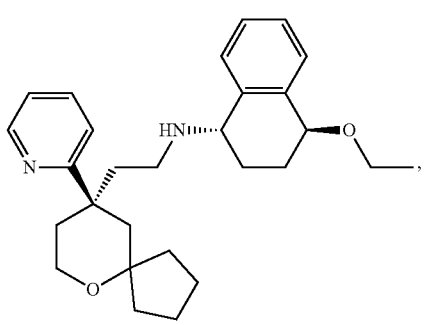

In some embodiments, the compound represented by formula I is shown as follows,

The present disclosure also provides a method for preparing a pharmaceutically acceptable salt of the compound represented by formula I, formula II, formula III, or formula IV, which comprises the steps as described in the above embodiments, and a step of reacting the compound represented by formula I, formula II, formula III, or formula IV with an acid to give the pharmaceutically acceptable salt thereof; the acid is an organic acid or an inorganic acid, preferably an organic acid; the organic acid is selected from the group consisting of acetic acid, maleic acid, fumaric acid, tartaric acid, citric acid, methanesulfonic acid, benzenesulfonic acid and p-toluenesulfonic acid, preferably fumaric acid; the inorganic acid is selected from the group consisting of hydrochloric acid, hydrobromic acid, sulfuric acid and phosphoric acid.

Term: the "halogen or halogen atom" in the present disclosure refers to fluorine, chlorine, bromine, iodine, etc.

The "alkyl" in the present disclosure refers to a straight or branched alkyl group containing 1-20 carbon atoms, and includes, for example, "$C_{1-6}$ alkyl", "$C_{1-4}$ alkyl", etc. Specific examples include, but are not limited to, methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc.

The "alkenyl" in the present disclosure refers to a straight or branched group containing at least one double bond and 2-20 carbon atoms, and includes, for example, "$C_{2-6}$ alkenyl, $C_{2-4}$ alkenyl", etc. Examples of the alkenyl include, but are not limited to, vinyl, propenyl, 2-butenyl, 2-pentenyl, 3-pentenyl, 2-hexenyl, 3-hexenyl, etc.

The "haloalkyl" in the present disclosure refers to a group derived by replacing one or more than one hydrogen atoms attached to the "alkyl" with one or more than one "halogen atom", the "halogen atom" and "alkyl" are as defined above.

The "hydroxylalkyl or hydroxyalkyl" in the present disclosure refers to a group derived by replacing one or more than one hydrogen atoms attached to the "alkyl" with one or more than one "hydroxyl", the "alkyl" is as defined above.

The "alkoxy, haloalkoxy, alkylcarbonyl, alkoxycarbonyl, alkoxycarbonyl, carbonylalkoxy, alkylcarbonylamino, alkylaminocarbonyl, alkylamino, dialkylamino, alkylsulfonylamino or alkylsulfonyl" in the present disclosure refers to the substituent in the form of alkyl-O—, haloalkyl-O—, alkyl-C(O)—, alkyl-O—C(O)—, C(O)-alkyl-O—, alkyl-C (O)—NH—, alkyl-NH—C(O)—, alkyl-NH—, (alkyl)$_2$-N—, alkyl-S(O)$_2$—NH— or alkyl-S(O)$_2$—, wherein the "alkyl, haloalkyl" are as defined above.

The "oxo" in the present disclosure refers to =O.

The "cycloalkyl" in the present disclosure refers to a saturated or partially unsaturated monocyclic or polycyclic hydrocarbon substituent containing 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc., preferably cyclopropyl, cyclohexenyl. Polycyclic cycloalkyl includes a cycloalkyl containing a spiro ring, fused ring and bridged ring.

The "aryl" in the present disclosure refers to a 6 to 14 membered monocyclic ring or polycyclic fused ring (that is, each ring in the system shares an adjacent pair of carbon atoms with another ring), with only carbon atom as ring atoms, having a conjugated n-electron system, preferably 6 to 10 membered aryl, more preferably phenyl, naphthyl, dihydronaphthyl, tetrahydronaphthyl, indenyl or fluorenyl, and most preferably phenyl.

The "heterocyclyl" in the present disclosure refers to a saturated or partially unsaturated monocyclic or polycyclic hydrocarbon substituent containing 3 to 20 ring atoms, wherein at least one ring atom is heteroatom, e.g. N, O or S, and the remaining ring atoms are C; optionally, the ring atoms (e.g., C, N or S) constituting the cyclic structure can be oxidized. Preferably, the heterocyclyl contains 3 to 12 ring atoms or 5 to 12 ring atoms wherein 1-4 ring atoms are heteroatoms; more preferably, the heterocyclyl contains 3 to 8 ring atoms, and most preferably 5 to 6 ring atoms. Non-limiting examples of monocyclic heterocyclyl include pyrrolidinyl, piperidinyl, piperazinyl, morpholinyl, thiomorpholinyl, homopiperazinyl, pyranyl, dihydrofuranyl, tetrahydrofuranyl, etc. Polycyclic heterocyclyl includes heterocyclyl containing a spiro ring, fused ring or bridged ring.

The "heteroaryl" in the present disclosure refers to a 5 to 14 membered aryl group having 1 to 4 heteroatoms as ring atoms, and the remaining ring atoms are C, wherein the heteroatom includes O, S or N. The heteroaryl is preferably 5 to 10 membered heteroaryl, more preferably 5 to 6 membered heteroaryl, specific examples include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, indolinyl, 2-pyridonyl, 4-pyridonyl, pyrimidinyl, pyridazinyl, pyrazinyl, 1,2,3-triazinyl, 1,3,5-triazinyl, 1,2,4,5-tetrazinyl azacycloheptatrienyl, 1,3-diazacycloheptatrienyl, azacyclooctatetraenyl, etc. The heteroaryl can also be fused to an aryl, heterocyclyl or cycloalkyl.

The "C, N or S is oxidized" in the present disclosure means forming the structure C=O, N=O, S=O or SO$_2$.

The "alcohol solvent" in the present disclosure refers to a group derived by substituting one or more than one hydrogen atoms attached to "C$_{1-6}$ alkyl" with one or more than one "hydroxyl", the "hydroxyl" and "C$_{1-6}$ alkyl" are as defined above; specific examples include, but are not limited to, methanol, ethanol, isopropanol, n-propanol, isopentanol or trifluoroethanol.

The "stereoisomerism" described in the present disclosure is classified into conformational isomerism and configurational isomerism, and configurational isomerism is further classified into cis-trans isomerism and optical isomerism (or enantiomerism). Conformational isomerism is a form of stereoisomerism in which rotations or distortions of single C—C bonds result in different spatial arrangements of atoms or atomic groups in an organic molecule with a certain configuration, commonly in alkane and cycloalkane compounds, such as cyclohexane conformations with chair and boat conformers. "Optical isomers (or enantiomers)" means that, when the compounds of the present disclosure have one or more than one asymmetry centers, and thus can be racemes and racemic mixtures, single enantiomers, diastereoisomer mixtures, and single diastereoisomers. The compounds of the present disclosure have asymmetry centers, which each independently lead to two optical isomers. The scope of the present disclosure includes all possible optical isomers and diastereoisomer mixtures, as well as pure or partially pure compounds. If the compounds of the present disclosure have alkene double bonds, unless otherwise specified, the compounds of the present disclosure include cis-isomers and trans-isomers. The compounds of the present disclosure can be present in form of tautomers, which have different hydrogen connection sites due to one or more than one double-bond shifts. For example, ketone and its enol form are keto-enol tautomers. Various tautomers and mixtures thereof are all included in the present disclosure. All the enantiomers, diastereoisomers, racemes, mesomers, cis-trans isomers, tautomers, geometric isomers, epimerides, and mixtures thereof fall into the scope of the present disclosure.

The structures of the compounds were identified by nuclear magnetic resonance (NMR) and/or mass spectrometry (MS). NMR shifts are given in 10-6 (ppm). NMR was determined by a Bruker AVANCE-400 nuclear magnetic resonance spectrometer, the solvents for determination were deuterated reagents and the internal standard was tetramethyl silane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatograph spectrometer and a Waters 2695-2996 high pressure liquid chromatography spectrometer, with octadecylsilane bonded silica gel as the column packing.

DETAILED DESCRIPTION OF THE PREFERRED EMBODIMENT

The following embodiments further illustrate the present disclosure, but the present disclosure is not limited thereto.

2-(9-(Pyridin-2-yl)-6-oxaspiro[4.5]decan-9-yl)acetonitrile (represented by formula (E1)) was prepared according to the method disclosed in patent application WO2012129495A1 (publication date 2012 Sep. 27),

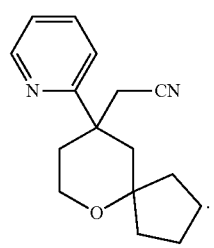

(E1)

Embodiment 1: Preparation of (1S,4S)-4-ethoxy-N-(2-((R)-9-(pyridin-2-yl)-6-oxaspiro[4.5]decan-9-yl)ethyl)-1,2,3,4-tetrahydronaphthalen-1-amine

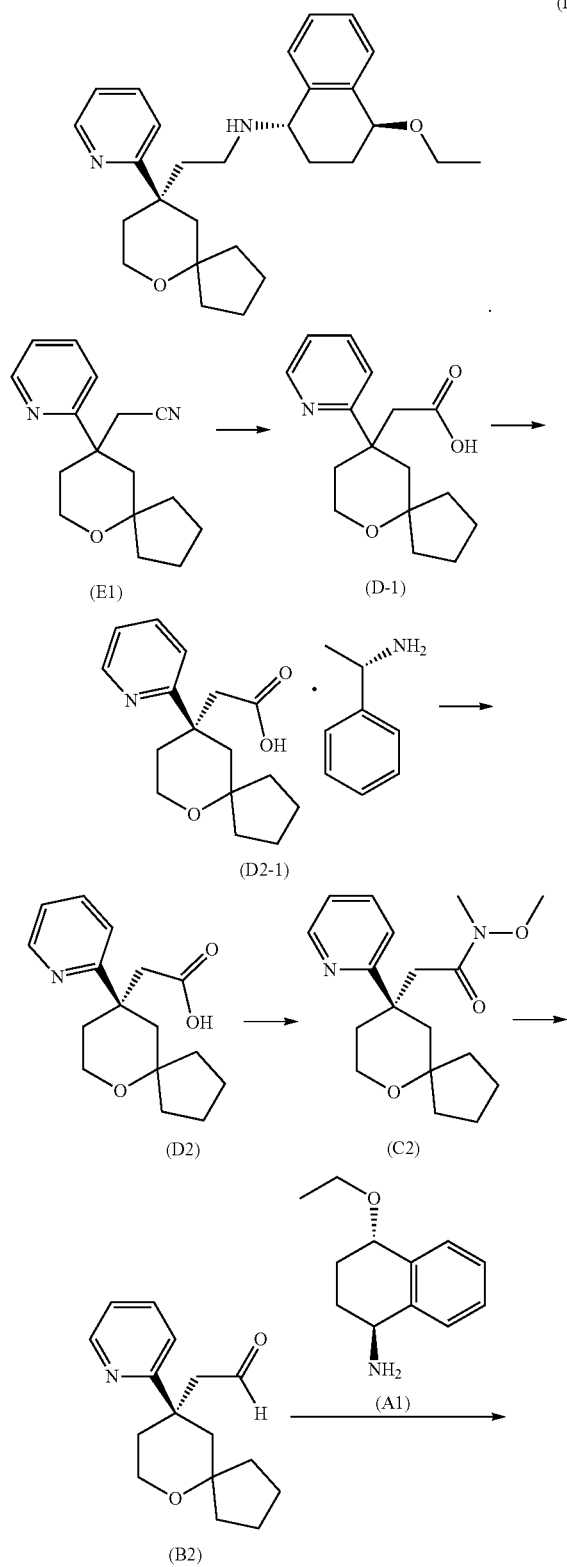

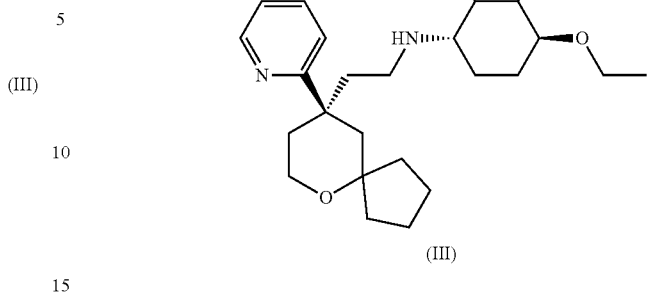

Step One: Synthesis of Intermediate (D-1)

The compound represented by the formula (E1) (25 g), potassium hydroxide (22.4 g) and ethylene glycol (150 mL) were mixed and the resulting mixture was stirred at 150° C. for 16 hours, and then the reaction was stopped. The reaction solution was cooled to room temperature, diluted with water (150 mL) and extracted with dichloromethane (150 mL×2). The aqueous phase was adjusted to pH=6-7 with 3M hydrochloric acid and extracted with dichloromethane (200 mL×4). The combined organic phase was washed with saturated sodium chloride solution (200 mL), dried over anhydrous sodium sulfate and filtered. The filtrate was concentrated under reduced pressure to give the product (26.1 g, pale yellow oil) with a yield of 97.4% and a HPLC purity of 92%.

Step Two: Synthesis of Intermediate (D2-1)

The compound represented by the formula (D-1) (28 g) was dissolved in anhydrous ethanol (100 mL) and the temperature was raised to 50° C. The resolving agent S-phenylethylamine (6.2 g) was dissolved in anhydrous ethanol (100 mL) and the resulting S-phenylethylamine solution was added dropwise into the above solution at 50° C. The mixture was heated to reflux and stirred for 2 hours. Then the mixture was allowed to cool to 10° C. naturally, and solid was precipitated. The mixture was filtered, and the filter cake was washed to give the product (13 g, solid) with an enantiomeric excess (ee) value of 96.7%;

recrystallization: the obtained 13 g solid product was added to anhydrous ethanol (80 mL), heated to reflux and stirred for 6 hours. Then the mixture was naturally cooled to 10° C. and solid was precipitated. The mixture was filtered, the filter cake was washed and dried to give the product (10.6 g) with an ee value of 99.0%.

Step Three: Synthesis of Intermediate (D2)

KOH (2.18 g) was dissolved in water (120 mL), and then the compound represented by formula (D2-1) was dissolved in the solution. The mixture was extracted with dichloromethane (100 mL×3). The aqueous phase was adjusted to pH=6-7 with 1N HCl solution and then extracted with dichloromethane (150 mL×3). The combined organic phase was dried over anhydrous sodium sulfate and filtered. The filtrate was concentrated under reduced pressure to give the product (7 g) with a yield of 50% and an ee value of 99.4%.

MS m/z (ESI): 276.71 [M+H]$^+$, 298.68 [M+Na]$^+$.

$^1$H NMR (400 MHz, CDCl$_3$) δ 8.50-8.51 (m, 1H), 7.73-7.77 (m, 1H), 7.51-7.53 (d, 1H), 7.21-7.24 (m, 1H), 3.73-3.84 (m, 2H), 2.78-2.81 (d, 1H), 2.58-2.63 (m, 1H), 2.53-2.56 (d, 1H), 2.39-2.43 (m, 1H), 1.98-2.02 (d, 1H), 1.87-1.94 (m, 1H), 1.76-1.80 (m, 1H), 1.61-1.65 (m, 1H), 1.39-1.58 (m, 4H), 1.14-1.19 (m, 1H), (m, 1H), (m, 1H).

Step Four: Synthesis of Intermediate (C2)

Dichloromethane (8.5 kg) was added to a reaction flask, and then the raw material (R)-2-(9-(pyridin-2-yl)-6-oxaspiro[4.5]decan-9-yl)acetic acid (350 g), N,O-dimethylhydroxylamine hydrochloride (148.8 g), EDCI (292.3 g) and DMAP (15.5 g) were added under stirring. After the resulting mixture was stirred for 15-25 minutes, DIPEA (492.4 g) was added. Then the mixture was stirred under argon protection at room temperature for 16-18 hours. A saturated ammonium chloride aqueous solution (2.8 kg) was added to the reaction solution, and the resulting mixture was stirred for 5-10 minutes and partitioned. The organic phase was washed with saturated ammonium chloride aqueous solution (2.8 kg×2) and saturated brine (2.7 kg), dried over anhydrous sodium sulfate and filtered. The filtrate was concentrated to dryness under reduced pressure and then dichloromethane (2.5 kg) was added. The mixture was concentrated to dryness under reduced pressure to give an oil (372.03 g) with a yield of 92.0%.

MS m/z (ESI): 319.1 [M+H]$^+$, 341.3 [M+Na]$^+$.

$^1$H NMR (400 MHz, CDCl$_3$) δ 8.50-8.51 (m, 1H), 7.66-7.71 (m, 1H), 7.43-7.45 (d, 1H), 7.15-7.18 (m, 1H), 3.63-3.66 (m, 2H), 3.47 (s, 3H), 2.86-2.88 (d, 3H), 2.62-2.65 (d, 1H), 2.50-2.57 (m, 1H), 2.36-2.39 (d, 1H), 1.96-2.00 (d, 1H), 1.80-1.86 (m, 1H), 1.68-1.72 (m, 1H), 1.48-1.55 (m, 1H), 1.31-1.46 (m, 4H), 1.03-1.07 (m, 1H), 0.63-0.71 (m, 1H).

Step Five: Synthesis of Intermediate (B2)

The compound represented by formula (C2) (334.4 g) was dissolved in toluene (2.2 kg) in a reaction flask. The solution was cooled to −45° C. to −35° C. and purged with argon, and then red aluminum (348.76 g) was added dropwise while maintaining the temperature between −45° C. to −35° C. After completion of the addition, the reaction solution was stirred at −45° C. to −35° C. for 3-4 hours, and then 10% citric acid aqueous solution (1 kg) was added to the reaction solution at −45° C. to −35° C. Then concentrated hydrochloric acid solution was added to adjust the pH to 2-3, followed by addition of ethyl acetate (1.8 kg). The mixture was stirred and allowed to stand to partition. The aqueous phase was adjusted to pH=11-13 with 5N sodium hydroxide solution, and then extracted with dichloromethane (3.3 kg×2). The combined dichloromethane phase was washed with saturated sodium chloride solution (2.7 kg), dried over anhydrous sodium sulfate and filtered. The filtrate was concentrated under reduced pressure, and then dichloromethane (3.3 kg) was added. The mixture was concentrated again under reduced pressure to give a pale red oil, which was directly used in the next step.

Step Six: Synthesis of the Compound Represented by Formula (III)

The above oil was added to a reaction flask, followed by addition of dichloromethane (8.5 kg) and the compound represented by formula (A1) (134.56 g). The resulting mixture was stirred for 2-3 hours, followed by addition of sodium triacetoxyborohydride (373.86 g). The mixture was stirred at room temperature for 16-18 hours, followed by addition of saturated sodium carbonate solution (2.66 kg). Then the mixture was adjusted to pH=11-13 by addition of 5N sodium hydroxide aqueous solution and partitioned. The organic phase was washed with saturated ammonium chloride aqueous solution (2.83 kg) and saturated sodium chloride aqueous solution (2.74 kg), dried over anhydrous sodium sulfate and filtered. The filtrate was concentrated to dryness under reduced pressure, and then acetonitrile (120 g) was added. The mixture was stirred at room temperature for 16-18 hours to crystallize, and then filtered. The filter cake was dried to give the product (206.87 g) with a yield of 68.0%.

MS m/z (ESI): 435.3 [M+H]$^+$.

$^1$H NMR (400 MHz, CDCl$_3$) δ 9.74 (d, 1H), 9.58 (d, 1H), 8.94 (d, 1H), 8.37 (d, 1H), 7.94 (d, 1H), 7.67 (d, 1H), 7.52 (d, 1H), 7.47 (t, 1H), 4.46-4.49 (m, 1H), 4.30-4.33 (m, 1H), 3.84-3.87 (m, 1H), 3.66-3.70 (m, 2H), 3.53-3.56 (m, 2H), 2.82-2.85 (d, 2H), 2.67 (s, 2H), 2.39-2.41 (m, 4H), 2.30-2.33 (m, 4H), 1.85 (s, 2H), 1.48-1.52 (m, 6H), 1.27 (m, 3H).

Embodiment 2

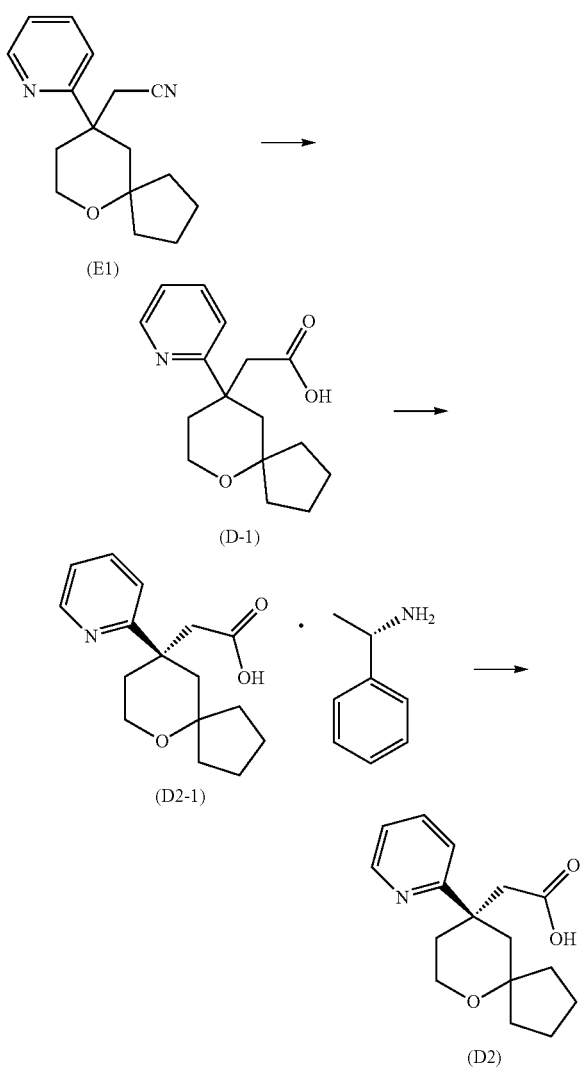

Step One: Synthesis of Intermediate (D-1)

The compound represented by the formula (E1) (13.5 kg, 1.0 eq), potassium hydroxide (2.6 kg, 2.0 eq) and ethylene glycol (135 L, 10 vol) were mixed, and the mixture was heated to 110° C. and stirred for 24 hours, and then the reaction was stopped. The resulting mixture was concentrated under reduced pressure to remove ethanol, then dichloromethane (26 L) was added to the residue and the mixture was stirred for dissolution. The mixture was washed twice with saturated sodium chloride solution (5 L), dried over anhydrous sodium sulfate and filtered. The filtrate was concentrated under reduced pressure to give the product (13 kg, yellow oil) with a yield of 90% and a HPLC purity of 95%.

Step Two: Synthesis of Intermediate (D2-1)

The product obtained from previous step (13 kg) was dissolved in ethylene glycol (65 L, 5 vol) and the temperature was raised to 50° C. The resolving agent S-phenylethylamine (5.7 kg, 1.0 eq) was dissolved in ethylene glycol (1 L) and the resulting S-phenylethylamine solution was added dropwise into the above solution at 50° C. The mixture was heated to reflux and stirred for 3 hours. Then the resulting mixture was allowed to cool to room temperature naturally, and solid was precipitated. The mixture was filtered, and the filter cake was washed to give the product (6600 g, solid);

recrystallization: the 6600 g solid was added into ethylene glycol (3 L), heated to reflux and stirred for 6 hours. Then the resulting mixture was naturally cooled to room temperature and solid was precipitated. The mixture was filtered, the filter cake was washed and dried to give the product (4700 g) with an ee value of 99.0%.

Step Three: Synthesis of Intermediate (D2)

The 4700 g solid was dissolved in water, and then 1.2 eq of potassium hydroxide was added and the resulting mixture was stirred for dissolution. The mixture was extracted with dichloromethane (DCM) (30 L×3). The organic phase was isolated, and the aqueous phase was adjusted to pH=6-7 with hydrochloric acid. Then the aqueous phase was extracted with DCM (30 L×5). The combined organic phase was dried and concentrated to give 200 g product with an ee value of 99.42% and a purity of 99%.

Although specific embodiments of the present disclosure are described above, those skilled in the art should understand that these are only examples for illustration, various modifications and changes can be made to the embodiments without departing from the principle and substance of the present disclosure. Thus the scope of the present disclosure is as defined in the claims attached herein.

What is claimed is:

1. A method for preparing a compound represented by formula D1 or a salt thereof,

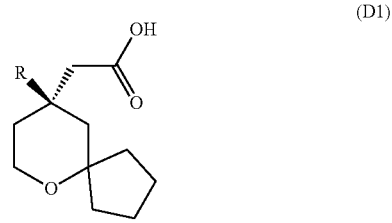

(D1)

comprising separating optical isomers of a compound represented by formula D or a salt thereof, by a chemical resolution method:

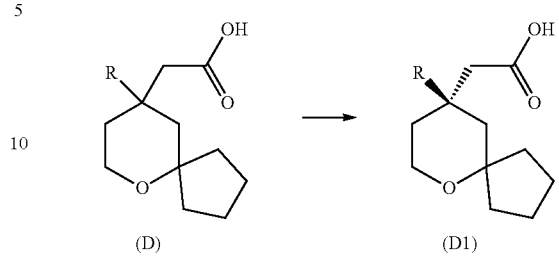

wherein,

R is aryl or heteroaryl, wherein the aryl or heteroaryl is optionally substituted by one or more substituents selected from the group consisting of alkyl, haloalkyl, halogen, amino, nitro, cyano, oxo, alkenyl, haloalkoxy, hydroxyalkyl, cycloalkyl, heterocyclyl, aryl, heteroaryl, $OR^3$, $C(O)R^3$, $C(O)OR^3$, $S(O)_mR^3$ and $NR^4R^5$;

$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are optionally substituted by one or more substituents selected from the group consisting of alkyl, halogen, hydroxyl, amino, nitro, cyano, alkoxy, hydroxyalkyl, cycloalkyl, heterocyclyl, aryl and heteroaryl;

each of $R^4$ and $R^5$ is independently selected from the group consisting of hydrogen, alkyl, alkoxy, hydroxyalkyl, hydroxyl, amino, carboxylic ester group, cycloalkyl, heterocyclyl, aryl and heteroaryl, wherein the alkyl, cycloalkyl, heterocyclyl, aryl and heteroaryl are optionally substituted by one or more substituents selected from the group consisting of alkyl, halogen, hydroxyl, amino, carboxylic ester group, nitro, cyano, alkoxy, hydroxyalkyl, cycloalkyl, heterocyclyl, aryl and heteroaryl; and m is 0, 1 or 2;

wherein a resolving agent is used in the chemical resolution method, and the resolving agent is a basic chiral resolving agent selected from the group consisting of S-phenylethylamine, quinidine, cinchonidine and arginine.

2. The method according to claim 1, further comprising preparing the compound represented by formula D from a compound represented by formula E by basic hydrolysis;

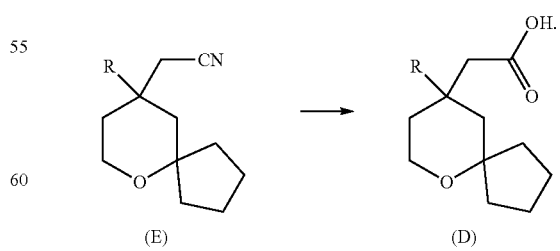

3. The method according to claim 1, wherein the compound represented by formula D1 is a compound represented by formula D2:

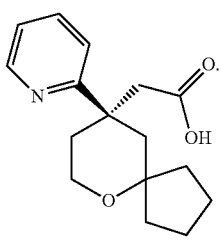

(D2)

4. The method according to claim 1, wherein the method comprises:

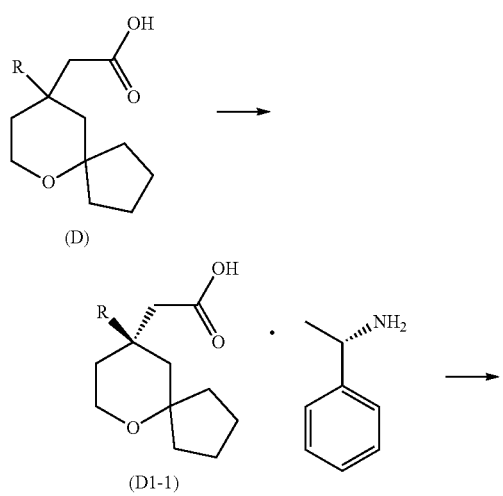

1) mixing the compound represented by formula D with S-phenylethylamine thereby to obtain a compound represented by formula D1-1; and
2) cleaving the compound represented by formula D1-1 to obtain the compound represented by formula D1.

5. A compound represented by formula D1 or a salt thereof,

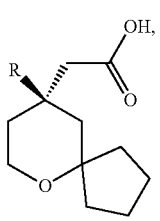

(D1)

wherein,

R is aryl or heteroaryl, wherein the aryl or heteroaryl is optionally substituted by one or more substituents selected front the group consisting of alkyl, haloalkyl, halogen, amino, nitro, cyano, oxo, alkenyl, haloalkoxy, hydroxyalkyl, cycloalkyl, heterocyclyl, aryl, heteroaryl, $OR^3$, $C(O)R^3$, $C(O)OR^3$, $S(O)_mR^3$ and $NR^4R^5$;

$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are optionally substituted by one or more substituents selected from the group consisting of alkyl, halogen, hydroxyl, amino, nitro, cyano, alkoxy, hydroxyalkyl, cycloalkyl, heterocyclyl, aryl and heteroaryl;

each of $R^4$ and $R^5$ is independently selected from the group consisting of hydrogen, alkyl, alkoxy, hydroxyalkyl, hydroxyl, amino, carboxylic ester group, cycloalkyl, heterocyclyl, aryl and heteroaryl, wherein the alkyl, cycloalkyl, heterocyclyl, aryl and heteroaryl are optionally substituted by one or more substituents selected from the group consisting of alkyl, halogen, hydroxyl, amino, carboxylic ester group, nitro, cyano, alkoxy, hydroxyalkyl, cycloalkyl, heterocyclyl, aryl and heteroaryl; and m is 0, 1 or 2;

and wherein the compound has an enantiomeric excess (ee) value of more than 99%.

6. The compound according to claim 5, wherein the compound is a compound represented by formula D2:

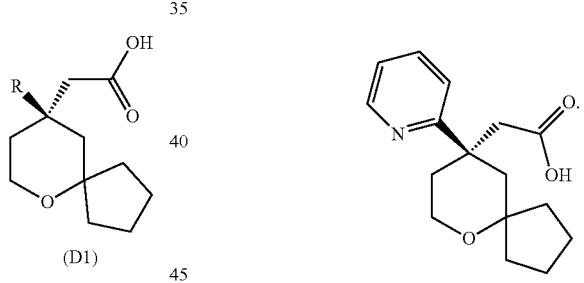

(D2)

7. The compound according to claim 5, wherein the salt of the compound is a compound represented by formula D1-1:

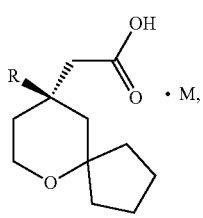

(D1-1)

wherein M is selected from the group consisting of S-phenylethylamine, quinidine, cinchonidine and arginine.

8. The method of claim 1,

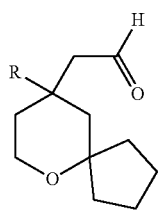

(B)

further comprising preparing a compound represented by formula B or a stereoisomer thereof from the compound represented by formula D or a stereoisomer thereof via an one-step reaction or a reaction of more than one step:

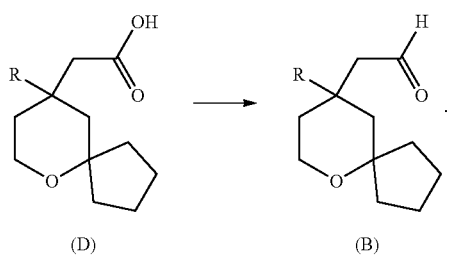

9. The method according to claim 8, wherein the method comprises:

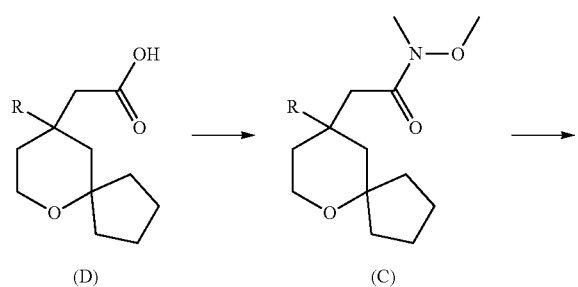

1) converting the compound represented by formula D to obtain a compound represented by formula C; and
2) reducing the compound represented by formula C thereby to obtain the compound represented by formula B:

wherein, R is

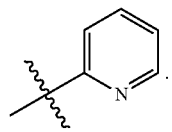

10. The method according to claim 8, wherein the compound represented by formula B is a compound represented by formula B2:

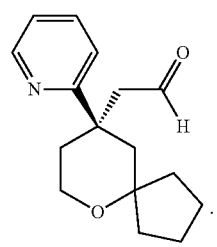

(B2)

11. The method according to claim 8, further comprising hydrolyzing a compound represented by formula E thereby to obtain the compound represented by formula D:

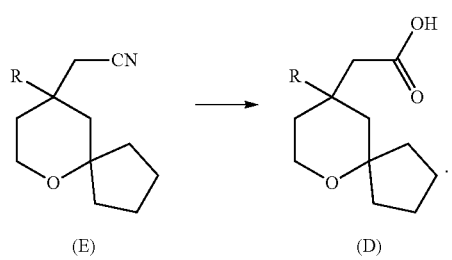

12. The method of claim 1, further comprising: reacting a compound represented by formula D or a stereoisomer thereof to prepare a compound represented by formula B or a stereoisomer thereof, and reacting the compound represented by formula B or a stereoisomer thereof with a compound represented by formula A or a stereoisomer thereof to obtain a compound represented by formula I,

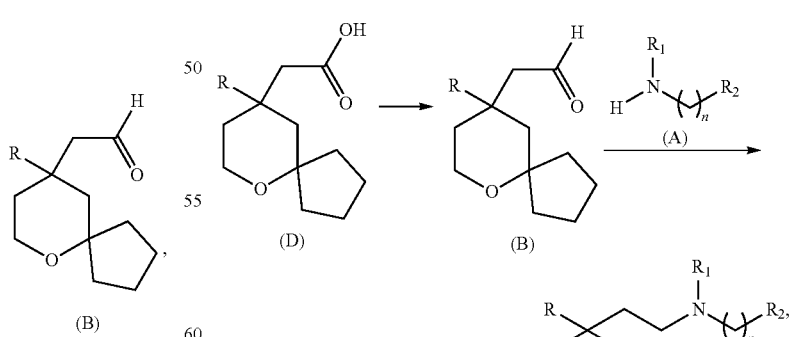

wherein,

R[1] is a hydrogen or an alkyl; R[2] is an optionally substituted aryl or heteroaryl, the substituent is selected from the group consisting of hydrogen, alkyl, haloalkyl, halogen, amino, nitro, cyano, oxo, alkenyl, haloalkoxy, hydroxyalkyl, cycloalkyl, heterocyclyl, aryl, heteroaryl, —OR[3], —C(O)R[3], —C(O)OR[3], —S(O)mR[3] and —NR[4]R[5], wherein the alkyl, alkoxy, alkenyl, haloalkyl, cycloalkyl, heterocyclyl, aryl and heteroaryl are optionally substituted by one or more substituents selected from the group consisting of deuterium, alkyl, haloalkyl, halogen, amino, nitro, cyano, hydroxyl, alkoxy, haloalkoxy, hydroxyalkyl, cycloalkyl, heterocyclyl, aryl and heteroaryl; and n is 0, 1, 2 or 3.

13. The method according to claim 12, wherein the compound represented by formula B is prepared by a method comprising:

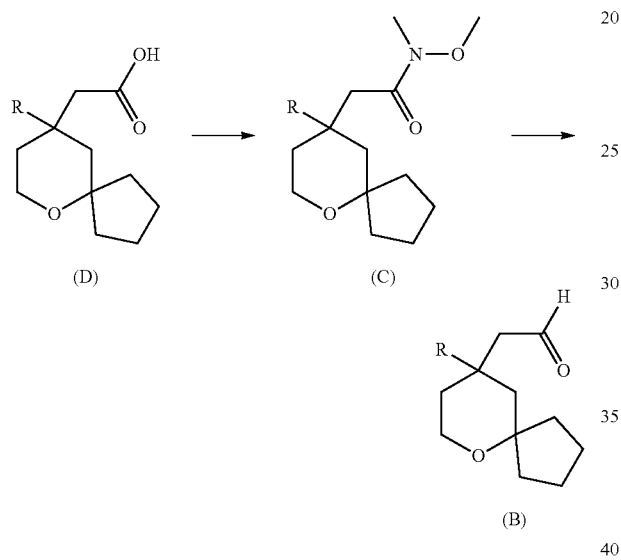

1) converting the compound represented by formula D to obtain a compound represented by formula C; and 2) reducing the compound represented by formula C thereby to obtain the compound represented by formula B.

14. The method according to claim 12, wherein the compound represented by formula I is a compound represented by formula III:

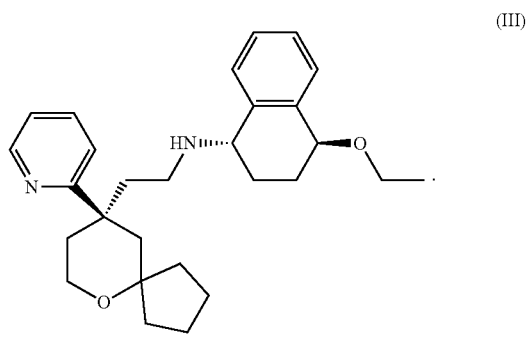 [SMILES: CCO[C@H]1CC[C@H](NCC[C@@]2(c3ccccn3)CCOC3(CCCC3)C2)c2ccccc21]

15. The method according to claim 12, wherein the compound represented by formula I is a compound represented by formula IV:

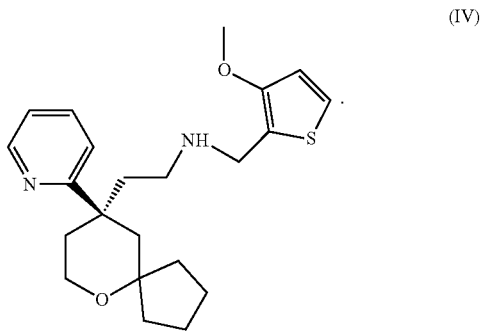 [SMILES: COc1ccsc1CNCC[C@@]1(c2ccccn2)CCOC2(CCCC2)C1]

* * * * *